US009200091B2

(12) United States Patent
German et al.

(10) Patent No.: US 9,200,091 B2
(45) Date of Patent: Dec. 1, 2015

(54) BOVINE MILK OLIGOSACCHARIDES

(75) Inventors: J. Bruce German, Davis, CA (US); David Mills, Davis, CA (US); Carlito B. Lebrilla, Davis, CA (US); Daniela Barile, Davis, CA (US); Riccardo LoCascio, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/809,556

(22) PCT Filed: Jul. 12, 2011

(86) PCT No.: PCT/US2011/043644
§ 371 (c)(1),
(2), (4) Date: Apr. 15, 2013

(87) PCT Pub. No.: WO2012/009315
PCT Pub. Date: Jan. 19, 2012

(65) Prior Publication Data
US 2013/0195803 A1    Aug. 1, 2013

Related U.S. Application Data

(60) Provisional application No. 61/363,432, filed on Jul. 12, 2010.

(51) Int. Cl.

| | |
|---|---|
| *A23L 1/29* | (2006.01) |
| *A23L 1/30* | (2006.01) |
| *A61K 31/702* | (2006.01) |
| *A61K 35/741* | (2015.01) |
| *A61K 35/745* | (2015.01) |
| *A61K 47/26* | (2006.01) |
| *C08B 37/00* | (2006.01) |
| *A61K 31/715* | (2006.01) |
| *C08L 5/00* | (2006.01) |
| *A61K 31/726* | (2006.01) |
| *C12P 19/14* | (2006.01) |
| *C12P 19/18* | (2006.01) |

(52) U.S. Cl.
CPC ............ *C08B 37/0063* (2013.01); *A23L 1/296* (2013.01); *A23L 1/3014* (2013.01); *A61K 31/715* (2013.01); *A61K 31/726* (2013.01); *A61K 35/741* (2013.01); *A61K 35/745* (2013.01); *C08B 37/0003* (2013.01); *C08B 37/006* (2013.01); *C08L 5/00* (2013.01); *C12P 19/14* (2013.01); *C12P 19/18* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2009/0098240 A1 | 4/2009 | Mills et al. | |
| 2011/0189342 A1* | 8/2011 | Jeong et al. | 426/42 |
| 2011/0256233 A1* | 10/2011 | Fournell et al. | 424/535 |

OTHER PUBLICATIONS

Girardet, J.-M. et al. 1995. Structure of glycopeptides isolated from bovine milk component PP3. European Journal of Biochemistry 234:939-946. specif. pp. 939-940, 943.*
Sigma-Aldrich. Concanavalin A-Agarose. Datasheet [online]. Sigma-Aldrich, Feb. 1, 2003 [retrieved on Nov. 9, 2013]. Retrieved from the Internet: <URL: http: www.sigmaaldrich.com/content/dam/sigma-aldrich/docs/Sigma/Product_Information_Sheet/c7555pis.pdf>.*
LoCascio, R.G. et al. 2007. Glycoprofiling of Bifidobacterial Consumption of Human Milk Oligosaccharides Demonstrates Strain Specific, Preferential Consumption of Small Chain Glycans Secreted in Early Human Lactation. Journal of Agricultural and Food Chemistry 55: 8914-8919. specif. pp. 8915, 8917-8918, incl. Supporting Online Material, pp. 1-3.*
Ninonuevo, M.R. et al. 2006. A Strategy for Annotating the Human Milk Glycome. Journal of Agricultural and Food Chemistry. 54: 7471-7480. specif. p. 7473.*
Natsuka, S. et al. 1994. Enzymes involved in mammalian oligosaccharide biosynthesis. Current Opinion in Structural Biology 4:683-691. specif. 683-684, 686.*
Nakajima et al.; "Capillary affinity electrophoresis using lectins for the analysis of milk oligosaccharide structure and its application to bovine colostrum oligosaccharides"; *Analytical Biochemistry*; 348:101-114 (2006).
Tao et al.; "Bovine Milk Glycome"; *Journal of Dairy Science*; 91 : 3768-3778 (2008).
The International Search Report from PCT/US2011/043644, dated Feb. 17, 2012 (4 pages).
The Extended European Search Report from EP 11807372.5, dated Mar. 28, 2014.
Biavati et al., "Bifidobacteria: history, ecology, physiology and applications," *Annals of Microbiology*, 2000, 50:117-131.
Biavati et al., "The Family Bifidobacteriaceae," *Prokaryotes*, 2006, 3:322-382.
Christiansen et al., "Chemical composition and nutrient profile of low molecular weight fraction of bovine colostrum," *International Dairy Journal*, 2010, 20(9):630-636.
Christiansen, S. (2010). Chemical Composition and Nutrient Profile of the Low Molecular Weight Fraction of Bovine Colostrum (Master's Thesis). Retrieved from the University of Vermont at website scholarworks.uvm.edu/cgi/viewcontent.cgi?article=1045 &context=graddis.
Coddeville et al., "Structure of the O-glycopeptides isolated from bovine milk component PP3," *Glycoconjugate Journal*, 1998, 15(4):371-378.
Kunz et al., "Oligosaccharides in Human Milk: Structural, Functional and Metabolic Aspects," *Ann. Rev. Nutr.*, 2000, 20:699-722.
Mattarelli et al., "Proposal to reclassify the three biotypes of *Bifidobacterium longum* as three subspecies: *Bifidobacterium longum* subsp. *longum* subsp. nov., *Bifidobacterium longum* subsp. *infantis* comb. nov. and *Bifidobacterium longum* subsp. *suis* comb. nov.," *International Journal of Systematic and Evolutionary Microbiology*, 2008, 58:767-772.
Mitsuoka, T., "Taxonomy and Ecology of Bifidobacteria," *Bifidobacteria Microflora*, 1984, 3(1):11-28.
Ward, R.E., "Isolation of Milk Oligosaccharides using Solid-Phase Extraction," *Open Glycoscience*, 2009, 2:9-15.

* cited by examiner

*Primary Examiner* — John S Brusca
*Assistant Examiner* — Sharon M Papciak
(74) *Attorney, Agent, or Firm* — Kilpatrick Townsend & Stockton LLP

(57) ABSTRACT

Oligosaccharides from bovine milk, whey and dairy products, and methods of producing bovine milk oligosaccharides are provided.

15 Claims, 4 Drawing Sheets

BOVINE MILK OLIGOSACCHARIDES

CROSS-REFERENCE TO RELATED PATENT APPLICATIONS

The present patent application is the US National Stage of International Application No. PCT/US2011/043644, filed Jul. 12, 2011, which claims benefit of priority to U.S. Provisional Patent Application No. 61/363,432, filed Jul. 12, 2011, each of which are incorporated by reference.

BACKGROUND OF THE INVENTION

Carbohydrates on human intestinal cell surface are important recognition sites for pathogenic bacterial binding that initiates infection. They are also the major components of human milk oligosaccharides (HMO). Depending on the lactation cycle, human milk contains >4 g/L of these complex and heterogeneous mixture of oligosaccharides [1]. HMO are composed by serial arrangement of D-glucose, D-galactose, N-acetylglucosamine, L-fucose and N-acetylneuraminic acid (Neu5Ac). Despite this large combinatorial potential human milk contains just over 200 oligosaccharides [1]. HMO contain a Lactose (Galβ1-4Glc) moiety at their reducing end with lactoN-biose I units (LNB; Galβ1-3GlcNAc) or lactosamine (Galβ1 4GlcNAc) elongated from a B1-3 or B1-6 linkage to the lactosyl terminus. A peculiar characteristic of HMO is their terminal fucosylation via α1-2/3/4 linkages and/or by α2-3/6 sialylation. In the absence of fucosidase and sialidase activities, these residues obstruct HMO core structures from microbial fermentation. HMO are not digested by infant gastrointestinal enzymes and remain largely intact until they reach the large intestine, where they can be used as fermentable substrate by the resident bacteria. One of their functions is to act as selective substrate to stimulate the colonic growth and proliferation of specific bacteria, such as Bifidobacteria [2].

HMOs are a class of indigestible oligosaccharides functioning as prebiotics, or "selectively fermented ingredients that allow specific changes, both in the composition and/or activity in the gatrointestinal microbiota that confers benefits upon host well-being and health" [3]. The large intestine of breast-fed infants is continuously exposed to copious amounts of HMO from mothers' milk and is characterized by a microbiota dominated by bifidobacterial species. The role of HMO is to selectively nourish the growth of specific strains of bifidobacteria priming the development of a unique gut microbiota in breast milk fed infants [4, 5, 6].

Recent studies investigating the catabolism and fermentation of HMOs by individual strains of infant-borne bifidobacteria have shown that *Bifidobacterium longum* subsp. *infantis* can grow extensively on HMOs as a sole carbon source, while adult-borne bifidobacterial species exhibited a more restricted growth profile [26]. Not all Bifidobacteria can grow on HMOs, for example within the closely related *B. longum* subspecies only strains belonging to subsp. *infantis* are capable of growth on HMOs. Limited HMO capacity has been shown for *B. bifidum*, while *B. adolescentis* and *B. animalis* subsp. *lactis* are unable to metabolize these complex oligosaccharides. These results suggest that HMOs may selectively promote the growth of certain bifidobacterial strains in the colonic lumen frequently isolated from breast-fed infants [23, 24].

It has been recently shown that compared to their nonautistic siblings, the fecal microbiome of children with Autism Spectrum Disorders (ASD) contain increased diversity of *Clostridia* spp. and higher cell counts of *Clostridium histolyticum* group [9]. The lack of a highly specific prebiotic, substrates, such as HMO, has hindered the development of infants and children's therapies to displace *Clostridia* spp. populations with beneficial, non-pathogenic Bifidobacteria spp. populations.

Enteric infections are responsible for ~2.1 million deaths per year and are the leading cause of children and infant mortality in developing countries [10]. Frequent occurrences of diarrhea are common among C-section, preterm, and formula-fed infant populations, and their cost on the healthcare system is between $400 and $1600 per infant treated [11, 12]. Exclusively breastfed infants possessing a bifidobacteria-rich infant colonic microbiota have dramatically lower rates of enteric infections, necrotizing enterocolitis (NEC), and gastroenteritis [11, 13, 14]. There is strong evidence for the use of probiotics and Bifidobacteria to prevent NEC in preterm infants [15].

Fucosylated oligosaccharides are abundant in human milk [16] and are known to inhibit the binding of pathogenic bacteria. HMO and in particular the fucosylated HMOs, share common structural motifs with glycans on the infant's intestinal epithelia known to be receptors for pathogens. Such structures imply that their presence in milk provides its host with a defensive strategy, with a 1,2-fucosylated HMO acting as a barrier to prevent binding of pathogens such as *Campylobacter jejuni* and caliciviruses to epithelial cells, thereby protecting infants from disease [4, 17]. HMOs, and in particular fucosylated HMOs are important functional constituent of human breast milk, and hold the promise for their use as a class of active ingredients for therapeutics specifically aimed at improving gut health. Unfortunately to date, a source of fucosylated oligosacchardes similar to those in human milk remains yet to be identified, for example bovine milk has been thought to be rich in sialylated oligosaccharides but not fucosylated ones. Interestingly, human milk only contains only about 20% of sialylated oligosaccharides.

At present, the only source of HMO is human milk, and the structural complexity of these oligosaccharides has hindered their commercial production. Attempts of reproducing HMO include the chemical synthesis of 2'- and 3'-Fucosyllactose as described in WO/2005/055944, and in transgenic non-human mammals (U.S. Pat. No. 5,750,176).

Milk oligosaccharides have also been characterized in domesticated animals including cow and goat, although they are generally lower in abundance and vary in prevalence of specific oligosaccharide compositions. An important distinction between human milk and other domesticated animals is the presence in the latter of N-glycolylneuraminic acid residues, these are absent in HMO consistent with the lost the ability of humans to synthesize this sialic acid [18]. These sources of milk oligosaccharides are therefore not suitable prebiotic oligosaccharides.

Prebiotics used to mimic the prebiotic effect of HMO include fruto-oligosaccharides (FOS), extracted from chicory roots and galacto-oligosaccharides (GOS) enzymatically synthesized from dairy-derived galactose [74]. FOS is broadly bifidogenic and is utilized by most bifidobacteria. FOS and GOS are added to some infant formulas (e.g. Similac Early Shield in the U.S.), and have found use as prebiotics in a wide range of food products. However these prebiotics lack the structural complexity of HMOs, such as the presence of terminal fucose or sialic acid moieties, and therefore unlikely provide the full spectrum of bioactivities of HMOs. FOS and GOS are therefore unlikely to retain the immunological and pathogen inhibition functions of HMOs. Moreover, current nutraceutical milk oligosaccharide mimetics, such as GOS and FOS do not reflect the genomic and physiological links between infant-type bifidobacteria and HMO; instead they target the bifidobacterial population nonspecifically.

There are currently no prebiotic oligosaccharides that can fully mimic the biological, structural, and glycomic functionalities of HMO. Analogues and mimics of HMOs could protect the mucosal surfaces in the infant gastrointestinal tract from pathogens, while at the same time act as a highly selective prebiotic substrate to target specific infant-type bifidobacteria) populations, such as the presence of terminal fucose or sialic acid moieties, and therefore unlikely provide the full spectrum of bioactivities of HMOs.

BRIEF SUMMARY OF THE INVENTION

The present invention provides for purified or isolated oligosaccharides (e.g., from a dairy source), wherein the oligosaccharide is from Table 1 and is selected from the group consisting of:
  an oligosaccharide consisting of 3 Hexose (Hex) moieties and 6 N-acetyl hexosamine (HexNAc) moieties;
  an oligosaccharide consisting of 4 Hex moieties and 3 HexNAc moieties;
  an oligosaccharide consisting of 3 Hex moieties and 4 HexNAc moieties;
  an oligosaccharide consisting of 6 Hex moieties and 2 HexNAc moieties;
  an oligosaccharide consisting of 3 Hex moieties, 4 HexNAc moieties and 1 fucose (Fuc) moiety; an oligosaccharide consisting of 4 Hex moieties and 4 HexNAc moieties;
  an oligosaccharide consisting of 3 Hex moieties and 5 HexNAc moieties;
  an oligosaccharide consisting of 4 Hex moieties, 4 HexNAc moieties, and 1 Fuc moiety;
  an oligosaccharide consisting of 5 Hex moieties and 4 HexNAc moieties;
  an oligosaccharide consisting of 3 Hex moieties, 5 HexNAc moieties, and 1 Fuc moiety;
  an oligosaccharide consisting of 4 Hex moieties and 5 HexNAc moieties;
  an oligosaccharide consisting of 3 Hex moieties and 6 HexNAc moieties;
  an oligosaccharide consisting of 5 Hex moieties, 4 HexNAc moieties, and 1 Fuc moiety;
  an oligosaccharide consisting of 4 Hex moieties, 5 HexNAc moieties, and 1 Fuc moiety; and
  an oligosaccharide consisting of 3 Hex moieties, 6 HexNAc moieties, and 1 Fuc moiety.

For convenience, the above-listed oligosaccharides can be further described by their sodiated m/z ratio as follows (more detail is provided in Table 1):
  an oligosaccharide having a charge/mass (m/z) ratio of about 1745.228 (sodiated mass), the oligosaccharide consisting of 3 Hex moieties and 6 HexNAc moieties;
  an oligosaccharide having a charge/mass (m/z) ratio of about 1298.241 (sodiated mass), the oligosaccharide consisting of 4 Hex moieties and 3 HexNAc moieties;
  an oligosaccharide having a charge/mass (m/z) ratio of about 1339.253 (sodiated mass), the oligosaccharide consisting of 3 Hex moieties and 4 HexNAc moieties;
  an oligosaccharide having a charge/mass (m/z) ratio of about 1419.225 (sodiated mass), the oligosaccharide consisting of 6 Hex moieties and 2 HexNAc moieties;
  an oligosaccharide having a charge/mass (m/z) ratio of about 1485.256 (sodiated mass), the oligosaccharide consisting of 3 Hex moieties, 4 HexNAc moieties and 1 fucose (Fuc) moiety;
  an oligosaccharide having a charge/mass (m/z) ratio of about 1501.529 (sodiated mass), the oligosaccharide consisting of 4 Hex moieties and 4 HexNAc moieties;
  an oligosaccharide having a charge/mass (m/z) ratio of about 1542.251 (sodiated mass), the oligosaccharide consisting of 3 Hex moieties and 5 HexNAc moieties;
  an oligosaccharide having a charge/mass (m/z) ratio of about 1647.240 (sodiated mass), the oligosaccharide consisting of 4 Hex moieties, 4 HexNAc moieties, and 1 Fuc moiety;
  an oligosaccharide having a charge/mass (m/z) ratio of about 1663.221 (sodiated mass), the oligosaccharide consisting of 5 Hex moieties and 4 HexNAc moieties;
  an oligosaccharide having a charge/mass (m/z) ratio of about 1688.24 (sodiated mass), the oligosaccharide consisting of 3 Hex moieties, 5 HexNAc moieties, and 1 Fuc moiety;
  an oligosaccharide having a charge/mass (m/z) ratio of about 1704.23 (sodiated mass), the oligosaccharide consisting of 4 Hex moieties and 5 HexNAc moieties;
  an oligosaccharide having a charge/mass (m/z) ratio of about 1809.21 (sodiated mass), the oligosaccharide consisting of 5 Hex moieties, 4 HexNAc moieties, and 1 Fuc moiety;
  an oligosaccharide having a charge/mass (m/z) ratio of about 1850.227 (sodiated mass), the oligosaccharide consisting of 4 Hex moieties, 5 HexNAc moieties, and 1 Fuc moiety; and
  an oligosaccharide having a charge/mass (m/z) ratio of about 1891.225 (sodiated mass), the oligosaccharide consisting of 3 Hex moieties, 6 HexNAc moieties, and 1 Fuc moiety.

The present invention also provides for compositions comprising a purified oligosaccharide (e.g., from a dairy source), wherein the oligosaccharide is selected from the group consisting of:
  an oligosaccharide consisting of 3 Hexose (Hex) moieties and 6 N-acetyl hexosamine (HexNAc) moieties;
  an oligosaccharide consisting of 4 Hex moieties and 3 HexNAc moieties;
  an oligosaccharide consisting of 3 Hex moieties and 4 HexNAc moieties;
  an oligosaccharide consisting of 6 Hex moieties and 2 HexNAc moieties;
  an oligosaccharide consisting of 3 Hex moieties, 4 HexNAc moieties and 1 fucose (Fuc) moiety;
  an oligosaccharide consisting of 4 Hex moieties and 4 HexNAc moieties;
  an oligosaccharide consisting of 3 Hex moieties and 5 HexNAc moieties;
  an oligosaccharide consisting of 4 Hex moieties, 4 HexNAc moieties, and 1 Fuc moiety;
  an oligosaccharide consisting of 5 Hex moieties and 4 HexNAc moieties;
  an oligosaccharide consisting of 3 Hex moieties, 5 HexNAc moieties, and 1 Fuc moiety;
  an oligosaccharide consisting of 4 Hex moieties and 5 HexNAc moieties;
  an oligosaccharide consisting of 3 Hex moieties and 6 HexNAc moieties;
  an oligosaccharide consisting of 5 Hex moieties, 4 HexNAc moieties, and 1 Fuc moiety;
  an oligosaccharide consisting of 4 Hex moieties, 5 HexNAc moieties, and 1 Fuc moiety; and
  an oligosaccharide consisting of 3 Hex moieties, 6 HexNAc moieties, and 1 Fuc moiety.

In some embodiments, the composition comprises at least two (e.g., at least 2, at least 3, at least 4, at least 5, at least 6, at least 7, at least 8, at least 9, etc.) oligosaccharides selected from selected from the group consisting of:

an oligosaccharide consisting of 3 Hexose (Hex) moieties and 6 N-acetyl hexosamine (HexNAc) moieties, an oligosaccharide consisting of 4 Hex moieties and 3 HexNAc moieties;

an oligosaccharide consisting of 3 Hex moieties and 4 HexNAc moieties;

an oligosaccharide consisting of 6 Hex moieties and 2 HexNAc moieties;

an oligosaccharide consisting of 3 Hex moieties, 4 HexNAc moieties and 1 fucose (Fuc) moiety;

an oligosaccharide consisting of 4 Hex moieties and 4 HexNAc moieties;

an oligosaccharide consisting of 3 Hex moieties and 5 HexNAc moieties;

an oligosaccharide consisting of 4 Hex moieties, 4 HexNAc moieties, and 1 Fuc moiety;

an oligosaccharide consisting of 5 Hex moieties and 4 HexNAc moieties;

an oligosaccharide consisting of 3 Hex moieties, 5 HexNAc moieties, and 1 Fuc moiety;

an oligosaccharide consisting of 4 Hex moieties and 5 HexNAc moieties;

an oligosaccharide consisting of 3 Hex moieties and 6 HexNAc moieties;

an oligosaccharide consisting of 5 Hex moieties, 4 HexNAc moieties, and 1 Fuc moiety;

an oligosaccharide consisting of 4 Hex moieties, 5 HexNAc moieties, and 1 Fuc moiety; and an oligosaccharide consisting of 3 Hex moieties, 6 HexNAc moieties, and 1 Fuc moiety.

In some embodiments, the composition comprises one or more of an oligosaccharide consisting of 3 Hex moieties, 4 HexNAc moieties and 1 fucose (Fuc) moiety;

an oligosaccharide consisting of 4 Hex moieties, 4 HexNAc moieties, and 1 Fuc moiety;

an oligosaccharide consisting of 3 Hex moieties, 5 HexNAc moieties, and 1 Fuc moiety;

an oligosaccharide consisting of 5 Hex moieties, 4 HexNAc moieties, and 1 Fuc moiety;

an oligosaccharide consisting of 4 Hex moieties, 5 HexNAc moieties, and 1 Fuc moiety; or an oligosaccharide consisting of 3 Hex moieties, 6 HexNAc moieties, and 1 Fuc moiety.

In some embodiments, the composition is a liquid and the content of the oligosaccharide in the composition is from 0.001-100 g/L or 0.05-10 g/L.

In some embodiments, the oligosaccharide content in the composition is from 0.5-1 g/L.

In some embodiments, the composition is a solid and the concentration of the oligosaccharide in the composition is from 100 micrograms/L to 25 grams/L.

In some embodiments, the composition is selected from the group consisting of a powder, a tablet, a capsule, a lozenge, a chewing gum, a food product, a supplemented beverage, a medical food, or a medical product.

In some embodiments, the composition further comprises a bovine milk protein, a soy protein, betalactoglobulin, whey, soybean oil or starch.

In some embodiments, said supplemented beverage is a member selected from the group consisting of an infant formula, follow-on formula, toddler's beverage, milk, fruit juice, and fruit-based drink.

In some embodiments, the oligosaccharide has been purified from bovine milk or a bovine milk product (including but not limited to whey).

In some embodiments, the composition further comprises an inoculum of a bacterium (e.g., a probiotic bacterium) or a fungus or yeast (e.g., a probiotic fungus or yeast). In some embodiments, the bacterium is a species of Bifidobacteria. In some embodiments, the bacterium is selected from *Bifidobacterium longum* subsp. *Infantis, B. breve*, and *B. bifidum*.

The present invention also provides methods of obtaining oligosaccharides. In some embodiments, the method comprises purifying oligosaccharides from bovine milk or a bovine milk product (including but not limited to whey), wherein the purifying comprises inactivating fucose-, sialic acid-, N-Acetylglucosamine-, lacto-N-biose-, glucose- and galactose-degrading enzymes in milk and/or separating the enzymes from oligosaccharides in the milk, thereby obtaining oligosaccharides. In some embodiments, the purified oligosaccharides comprise at least one or more oligosaccharide of Table 1.

The present invention also provides a method of obtaining the oligosaccharide(s) as described above, comprising purifying the oligosaccharide from bovine milk. In some embodiments, the purifying comprises separating fucose-, sialic acid-, N-Acetylglucosamine-, lacto-N-biose-, glucose- and galactose-degrading enzymes in milk from the oligosaccharide.

The present invention also provides methods of modifying the purified oligosaccharide(s) as described above, comprising contacting the oligosaccharide with at least one modifying enzyme, thereby adding or removing one or more chemical moiety from the purified oligosaccharide, thereby generating a modified oligosaccharide. In some embodiments, the modifying enzyme is selected from the group consisting of a fucosidase, fucosyltransferase, sialidase, sialyltransferase, a glycosidase, and a glycosyltransferase. In some embodiments, the method further comprises contacting the oligosaccharide with at least one modifying enzyme, thereby adding or removing a chemical moiety from the oligosaccharide, thereby generating a modified oligosaccharide. In some embodiments, the modifying enzyme is selected from the group consisting of a fucosidase, fucosyltransferase, sialidase, sialyltransferase, a glycosidase, and a glycosyltransferase. In some embodiments, the oligosaccharide comprises an HexNAc terminus and the modifying enzyme adds one, two or several GDP-Fucose moieties to the HexNAc terminus. In some embodiments, the oligosaccharide comprises an HexNAc terminus and the modifying enzyme adds one, two or several CMP-Sialic Acid moieties to the HexNAc terminus. In some embodiments, the oligosaccharide comprises a HexNAc-Fuc dimer and the modifying enzyme cleaves the dimer from the remainder of the oligosaccharide. In some embodiments, the remainder of the oligosaccharide is combined with galactooligosaccharides (GOS) and/or fructooligosaccharides (FOS) to form a prebiotic composition.

In some embodiments, the method further comprises formulating the oligosaccharide(s) or modified oligosaccharide(s) into a composition for human or animal consumption. In some embodiments, the food product is a powder, a tablet, a capsule, a lozenge, a chewing gum, a food product, a supplemented beverage, or a medical food.

The present invention also provides methods comprising administering an amount of the composition described above to an individual. In some embodiments, the method prevents, treats, or ameliorates a condition in the individual, the method comprising administering a sufficient amount of the composition to the individual to prevent, treat, or ameliorate the condition, wherein the individual has or is at greater risk that the general population of later having the condition, and the condition is selected from the group consisting of
  diarrhea;
  necrotizing enterocolitis;
  irritable bowel syndrome;
  allergic reaction;
  Autism Spectrum Disorder (ASD); and
  presence of *Enterococcus faecalis, Clostridium difficile* and *Salmonella enterica, Salmonella typhimurium, Vibrio cholerae, E. coli* O157:H7, *Clostridium perifringens, Vibrio cholerae, Listeria monocytogenes, Yersinia entercolitis, Enterococcus faecalis, Eubacteria rectales* other enteropathogenic bacteria, *Shigella* species in the individual.

In some embodiments, the oligosaccharide: selectively stimulates the production of a Bifidobacterial secretion that modulates gut health in the individual; improves at least one biomarker of gut health in the individual; or increases gut colonization and persistence of probiotic bacteria in the individual.

In some embodiments, the secretion is selected from the group consisting of an antibiotic, bacteriocin, protein, peptide, glycoprotein, glycopeptide, lipid, glycolipid, and an exopolysaccharide. These secretions can also modulate signals generated by enteroendocrine and gut epithelial cells with local and systemic effects on host health.

In some embodiments, the biomarker is a cytokine or chemokine. In some embodiments, the biomarker is an inflammatory cytokine or chemokine. In some embodiments, the cytokine is selected from the group consisting of IL-4, IL-1β, IL-6, TNF-α, IL-1β and INF-γ.

In some embodiments, the individual is a human. In some embodiments, the individual is a non-human animal.

In some embodiments, bacteria, yeast, or fungi is administered as part of or in conjunction with the composition. In some embodiments, the bacteria is a species of Bifidobacteria. In some embodiments, the bacteria is selected from the group consisting of *Bifidobacterium longum* subsp. *Infantis, B. breve*, and *B. bifidum*.

The present invention also provides methods comprising administering an amount of the composition as described above (i.e., comprising at least one oligosaccharide as described above purified from bovine milk or milk products) to an individual. In some embodiments, the method prevents, treats, or ameliorates a condition in the individual, the method comprising administering a sufficient amount of the composition to the individual to prevent, treat, or ameliorate the condition, wherein the individual has or is at greater risk that the general population of later having the condition, and the condition is selected from the group consisting of
  diarrhea;
  necrotizing enterocolitis;
  irritable bowel syndrome;
  allergic reaction;
  Autism Spectrum Disorder (ASD); and
  presence of *Enterococcus faecalis, Clostridium difficile* and *Salmonella enterica, Salmonella typhimurium, Vibrio cholerae, E. coli* O157:H7, *Clostridium perifringens, Vibrio cholerae, Listeria monocytogenes, Yersinia entercolitis, Enterococcus faecalis, Eubacteria rectales* other enteropathogenic bacteria, *Shigella* species in the individual.

In some embodiments, the oligosaccharide: selectively stimulates the production of a Bifidobacterial secretion that modulates gut health in the individual; improves at least one biomarker of gut health in the individual; or increases gut colonization and persistence of probiotic bacteria in the individual.

In some embodiments, the secretion is selected from the group consisting of an antibiotic, bacteriocin, protein, peptide, glycoprotein, glycopeptide, lipid, glycolipid, and an exopolysaccharide. These secretions can also modulate signals generated by enteroendocrine and gut epithelial cells with local and systemic effects on host health.

In some embodiments, the biomarker is a cytokine or chemokine. In some embodiments, the biomarker is an inflammatory cytokine or chemokine. In some embodiments, the cytokine is selected from the group consisting of IL-4, IL-1β, IL-6, TNF-α, IL-1β and INF-γ.

In some embodiments, the individual is a human. In some embodiments, the individual is a non-human animal.

In some embodiments, a bacteria is administered as part of or in conjunction with the composition. In some embodiments, the bacteria is a species of Bifidobacteria. In some embodiments, the bacteria is selected from the group consisting of *Bifidobacterium longum* sbsp. *infantis, B. brev*, and *B. bifidum*.

Other embodiments will be clear from a complete reading of this document.

DEFINITIONS

As used herein, the term "oligosaccharide" refers to polymeric carbohydrates that contain 3 to 20 monosaccharides covalently linked through glycosidic bonds. In some embodiments, the oligosaccharides are purified from bovine milk/whey/cheese/dairy products, e.g., purified away from oligosaccharide-degrading enzymes in bovine milk/whey/cheese/dairy products.

"Sodiated mass" refers to an oligosaccharide analyzed in the positive mode using sodium to form the adduct $(M+Na)^+$ (sodium=Na; m/z 22.989). Mass spectrometry analysis MALDi FT ICR of native (underivatized) glycans can be acquired using either positive or negative ions. Oligosaccharides carrying negative charges such as those containing N-acetylneuraminic acid (sialic acid) produce more intense signal in negative than positive ion-detection mode of analysis because they readily deprotonate forming $[M-H]^-$. Conversely, neutral oligosaccharides (the kind without sialic acid) are more difficult to detect in negative mode because their ionization efficiency is lower, in fact neutral oligosaccharides have a low tendency to form $[M-H]^-$. Therefore, to improve neutral oligosaccharides detection, a metal-carbohydrate adduct can be formed using sodium, and then performed the analyses in positive ion-detection mode, forming the adduct $[M+Na]^+$. Results from this assay produce sodiated m/z values (e.g., such as present in Table 1 below). The neutral mass is calculated from sodiated values by subtracting 22.989 units (MW of the sodium ion).

"Dairy" refers to milk or milk products or milk byproducts from a cow, goat, sheep, buffalo or other domesticated non-human mammal.

"Hexose (Hex)" represents a residue of glucose or galactose or mannose. These molecules have a monoisotopic m/z of 162.0528.

"Fucose (Fuc)" represents a residue of Deoxyhexose. This molecule has a monoisotopic m/z of 146.0579.

"HexNAc" represents a residue of N-acetylglucosamine or N-acetylgalactosamine. This molecule has a monoisotopic m/z of 203.0794.

"NeuAc" represents a residue of N-acetyl neuraminic acid (sialic acid). this molecule has monoisotopic m/z of 291.0954.

BRIEF DESCRIPTION OF THE DRAWINGS

FIG. 3 illustrates growth of select pathogens on BMO.

DETAILED DESCRIPTION

I. Introduction

Figure 1:
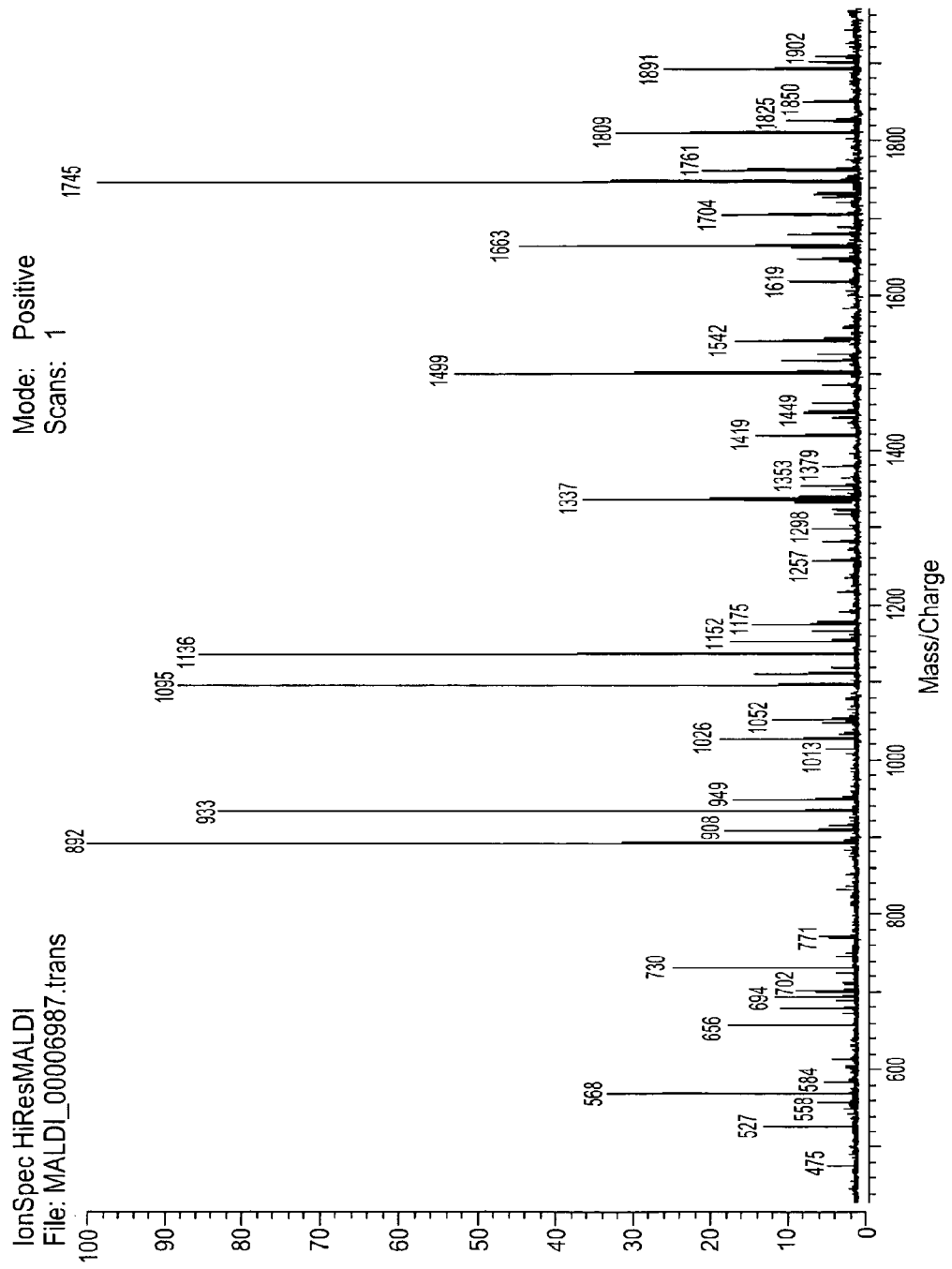
FIG. 1 illustrates a mass spectrum of purified oligosaccharides. The mass spectrum was recorded in positive ionization mode.

Methods for treating infections and increasing bifidobacteria populations using milk oligosaccharide analogues are provided. Analogues and mimics closely resembling the glycomic complexity of HMO would be the preferred prebiotic source for all infant nutritional products and would allow the health benefits that milk oligosaccharides provide for infants could also be made available to individuals of all ages. The inventors have surprisingly discovered that bovine milk contains a number of oligosaccharides that were previously not known to occur in bovine milk. Indeed, some of the oligosaccharides were not known before at all. More surprisingly, among these newly discovered oligosaccharides are a sub-set of oligosaccharides containing fucose. Purified oligosaccharides, compositions comprising the purified oligosaccharides and methods of purifying, manipulating and using the oligosaccharides and compositions are provided. In some embodiments, compositions described herein include one or more non-milk components, e.g., a non-milk protein, non-milk lipid, or non-milk carbohydrate.

The inventors have also found that enzymes naturally occur in milk that destroy the oligosaccharides described herein. Therefore, the inventors have discovered that the oligosaccharides can be purified by separating the oligosaccharides in bovine milk from the degrading enzymes, thereby allowing for the purification of the oligosaccharides from bovine milk. Therefore, methods of generating purified oligosaccharides from bovine milk are provided.

Notably, the inventors have also found that at least some of the discovered oligosaccharides are capable of selectively supporting growth of desirable ("probiotic") bacteria while not supporting growth of pathogenic bacteria. Thus, it is believed that the discovered oligosaccharides, as well as modified forms thereof, will be useful in preventing, treating, or ameliorating a large number of conditions for which probiotic bacterial growth is beneficial.

II. Oligosaccharides Identified in Bovine Milk Products (BMOs)

Table 1 summarizes the oligosaccharides identified in bovine milk and whey and provides the number of different monomeric units in the discovered oligosaccharides, their experimental charge-to-mass ratio using sodiated adducts (i.e. where sodium ions have been used to analyze oligosaccharides in positive ionization mode) and the neutral mass (calculated by subtracting the ion sodium) of the oligosaccharides analyzed by mass spectrometry, and their degree of polymerization (DP). The monomeric composition of sodiated parent ions was obtained by tandem collision-induced dissociation-mass spectrometry.

| Neutral Mass (m/z) Calculated | Sodiated m/z $[M + Na]^+$ Experimental | Hexose | HexNAc | Fucose | NeuAc | DP |
|---|---|---|---|---|---|---|
| 488.174 | 511.163 | 2 | 0 | 1 | 0 | 3 |
| 504.169 | 527.133 | 3 | 0 | 0 | 0 | 3 |
| 545.195 | 568.154 | 2 | 1 | 0 | 0 | 3 |
| 633.210 | 656.156 | 2 | 0 | 0 | 1 | 3 |
| 666.223 | 689.211 | 4 | 0 | 0 | 0 | 4 |
| 691.254 | 714.243 | 2 | 1 | 1 | 0 | 4 |
| 707.253 | 730.179 | 3 | 1 | 0 | 0 | 4 |
| 748.282 | 771.197 | 2 | 2 | 0 | 0 | 4 |
| 795.266 | 818.230 | 3 | 0 | 0 | 1 | 4 |
| 812.281 | 835.269 | 4 | 0 | 1 | 0 | 5 |
| 828.279 | 851.264 | 5 | 0 | 0 | 0 | 5 |
| 853.307 | 876.296 | 3 | 1 | 1 | 0 | 5 |
| 869.306 | 892.196 | 4 | 1 | 0 | 0 | 5 |
| 910.346 | 933.213 | 3 | 2 | 0 | 0 | 5 |
| 990.326 | 1013.317 | 6 | 0 | 0 | 0 | 6 |
| 1031.355 | 1054.343 | 5 | 1 | 0 | 0 | 6 |
| 1038.378 | 1061.238 | 2 | 2 | 0 | 1 | 5 |
| 1072.379 | 1095.219 | 4 | 2 | 0 | 0 | 6 |
| 1113.408 | 1136.234 | 3 | 3 | 0 | 0 | 6 |
| 1152.381 | 1175.37 | 7 | 0 | 0 | 0 | 7 |
| 1234.434 | 1257.229 | 5 | 2 | 0 | 0 | 7 |
| 1259.466 | 1282.454 | 3 | 3 | 1 | 0 | 7 |
| 1275.461 | 1298.241 | 4 | 3 | 0 | 0 | 7 |
| 1362.469 | 1385.433 | 4 | 2 | 0 | 1 | 7 |
| 1314.434 | 1337.193 | 8 | 0 | 0 | 0 | 8 |
| 1316.487 | 1339.253 | 3 | 4 | 0 | 0 | 7 |
| 1396.487 | 1419.225 | 6 | 2 | 0 | 0 | 8 |
| 1404.496 | 1427.455 | 3 | 3 | 0 | 1 | 7 |
| 1462.545 | 1485.256 | 3 | 4 | 1 | 0 | 8 |
| 1476.486 | 1499.184 | 9 | 0 | 0 | 0 | 9 |
| 1478.540 | 1501.529 | 4 | 4 | 0 | 0 | 8 |
| 1519.567 | 1542.251 | 3 | 5 | 0 | 0 | 8 |
| 1524.522 | 1547.559 | 5 | 2 | 0 | 1 | 8 |
| 1566.548 | 1589.507 | 4 | 3 | 0 | 1 | 8 |
| 1624.598 | 1647.240 | 4 | 4 | 1 | 0 | 9 |
| 1640.593 | 1663.221 | 5 | 4 | 0 | 0 | 9 |
| 1665.625 | 1688.24 | 3 | 5 | 1 | 0 | 9 |
| 1681.620 | 1704.23 | 4 | 5 | 0 | 0 | 9 |
| 1722.646 | 1745.228 | 3 | 6 | 0 | 0 | 9 |
| 1786.651 | 1809.21 | 5 | 4 | 1 | 0 | 10 |
| 1827.677 | 1850.227 | 4 | 5 | 1 | 0 | 10 |
| 1868.704 | 1891.225 | 3 | 6 | 1 | 0 | 10 |

"DP" refers to the degree of polymerization, i.e., the number of units (monosaccharides) of the oligosaccharide.

The present invention provides for one or more purified oligosaccharide as set forth in Table 1, as well as compositions containing the one or more purified oligosaccharides.

As shown in the Examples, each of the oligosaccharides described in Table 1 can be purified from bovine milk products, including but not limited to, milk, whey, cheese, and other dairy products. In view of the abundance of bovine milk and other dairy products in the world economy, it is anticipated that the most commercially-efficient way to produce the purified oligosaccharides described herein will be by purification from bovine milk and other dairy streams. Therefore, in some embodiments, a method of purifying an oligosaccharide, including but not limited to, one or more oligosaccharide as described in Table 1 is provided by purifying the oligosaccharide(s) from bovine milk. "Purified oligosaccharide" refers to an oligosaccharide that has been at least enriched for the oligosaccharide compared to one or more other ingredient in milk. In some embodiments, the oligosaccharide(s) is substantially purified, e.g., such that other non-oligosaccharides of milk are substantially absent. In some embodiments, at least one oligosaccharide in the purified composition is at a concentration of at least 0.001, 0.001, 0.1, 1, 10 or 100 g/L.

Bovine mammary glands contain several enzymes, called glycosidases, whose function is to gradually hydrolyze glycans (i.e. oligosaccharides) to smaller residues. High molecular weight oligosaccharides (including those containing fucose) are degraded to generate the corresponding smaller/core oligosaccharides that have been previously identified in bovine milk. Therefore the high molecular weight oligosaccharides as described in Table 1 are not readily detectable in liquid milk (e.g. store-bought liquid milk). In some embodiments, the method of purifying the oligosaccharide(s) from bovine milk comprises sequestering, separating, and/or inactivating the glycosidases and/or other fucose-, sialic acid-, N-Acetylglucosamine-, lacto-N-biose-, glucose- and galactose-degrading enzymes from the target oligosaccharide(s). This can be achieved, for example, by conventional filtration techniques of appropriate size to selectively remove these molecules from the remainder of the milk components using ultrafiltration membranes. In some embodiments the membranes used have a molecular weight cut off (MWCO) of 30 to 70 kDa. In some embodiments, the membranes have a MWCO of 40 to 50 kDa. Similarly, techniques such as dialysis, ultrafiltration combined with diafiltration allow for purification of the oligosaccharides in bovine milk as described herein.

Alternatively, enzymatic methods can be used to synthesize the oligosaccharides of the present invention. In general, any oligosaccharide biosynthetic enzyme or catabolic enzyme (with the reaction running in reverse) that converts a substrate into any of the oligosaccharide described herein (or their intermediates) may be used in the practice of this invention. In some embodiments the saccharidic components of milk oligosaccharides, such as glucose, galacatose, lactose, N-Acetylglucosamine, N-Acetylgalactosamine, Fucose, Sialic Acids can be combined by using glycosyltransferases to recreate analogues of human milk oligosaccharides.

Alternatively, conventional chemical methods may be used for the de novo organic synthesis of or conversion of pre-existing oligosaccharides into the oligosaccharides described herein. See, e.g., March's Advanced Organic Chemistry: Reactions, Mechanisms, and Structure, 5th Edition.

The purified oligosaccharides of the invention, whether purified from bovine milk or from synthesis reactions, can have any concentration as desired. In some embodiments, an oligosaccharide of Table 1 is at least 1, 10, 100 micrograms/L, or at least 1 gram or 10 gram/L. For example, in some embodiments, the oligosaccharides (i.e., a single oligosaccharide or a mixture of two or more oligosaccharides as found in Table 1) concentration is from 1, 10, 100 micrograms/L to 25 grams/L.

In some embodiments, oligosaccharides from a dairy product (e.g., milk) are selected for a particular degree of polymerization (DP). For example, in some embodiments, purified oligosaccharides are enriched for those having a DP of greater than 4, 5, 6, 7, 8, 9, 10, or more. In some embodiments, purified oligosaccharides are enriched for those having a DP between 3-10, 3-8, 4-8, 4-10, 5-10, 6-10, etc.

Selection of particular DPs can be achieved using any method available, for example, using solid-phase extraction. For instance, after filtering the milk/whey by membrane filtration, the oligosaccharides are purified from milk/whey by solid-phase extraction using nonporous graphitized carbon polypropylene cartridges. In some embodiments, the low mass oligosaccharides from DP 2 to DP 6 are eluted from the cartridges using an 90:10 deionized water—acetonitrile solution; and the high mass more complex oligosaccharides from DP 7 to DP 10 are sequentially eluted from the cartridges using an 80:20 deionized water—acetonitrile solution.

In some embodiments, the fucosylated oligosaccharides (for example, in one aspect from DP 7 to DP 10) are purified from a dairy product using an 80:20 deionized water—acetonitrile solution. Fucosylated oligosaccharides are of particular interest because in some embodiments they are structurally similar to human milk oligosaccharides.

III. BMO Formulations

The oligosaccharides compositions of the present invention can be administered, either as purified from milk or modified versions as discussed further below) as a prebiotic formulation (i.e., without bacteria) or as a synbiotic formulation (i.e., with desirable bacteria such as bifidobacteria as described herein). In general, any food or beverage that can be consumed by human infants or adults or animals may be used to make formulations containing the prebiotic and synbiotic compositions of the present invention. Exemplary foods include those with a semi-liquid consistency to allow easy and uniform dispersal of the prebiotic and synbiotic compositions of the invention. However, other consistencies (e.g., powders, liquids, etc.) can also be used without limitation. Accordingly, such food items include, without limitation, dairy-based products such as cheese, cottage cheese, yogurt, and ice cream. Processed fruits and vegetables, including those targeted for infants/toddlers, such as apple sauce or strained vegetables (e.g., peas and carrots, etc.), are also suitable for use in combination with the prebiotic and synbiotic compositions of the present invention. Both infant cereals such as rice- or oat-based cereals and adult cereals such as Musilix are also suitable for use in combination with the oligosaccharides of the present invention. In addition to foods targeted for human consumption, animal feeds may also be supplemented with the prebiotic and synbiotic compositions of the invention.

Alternatively, the prebiotic and synbiotic compositions of the invention can be used to supplement a beverage. Examples of such beverages include, without limitation, infant formula, follow-on formula, toddler's beverage, milk, fermented milk, fruit juice, fruit-based drinks, and sports drinks. Many infant and toddler formulas are known in the art and are commercially available, including, for example, Carnation Good Start (Nestle Nutrition Division; Glendale, Calif.) and Nutrish A/B produced by Mayfield Dairy Farms (Athens, Tenn.). Other examples of infant or baby formula include those disclosed in U.S. Pat. No. 5,902,617. Other beneficial formulations of the compositions of the present invention include the supplementation of animal milks, such as cow's milk.

Alternatively, the prebiotic and probiotic compositions of the present invention can be formulated into pills or tablets or encapsulated in capsules, such as gelatin capsules. Tablet forms can optionally include, for example, one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge or candy forms can comprise the compositions in a flavor, e.g., sucrose, as well as pastilles comprising the compositions in an inert base, such as gelatin and glycerin or sucrose and acacia emulsions, gels, and the like containing, in addition to the active ingredient, carriers known in the art. The prebiotic or synbiotic formulations may also contain conventional food supplement fillers and extenders such as, for example, rice flour.

In some embodiments, the prebiotic or synbiotic composition will further comprise a non-human protein, non-human lipid, non-human carbohydrate, or other non-human component. For example, in some embodiments, the compositions of the invention comprise a bovine (or other non-human) milk protein, a soy protein, a rice protein, betalactoglobulin, whey, soybean oil or starch. In some embodiments, the prebiotic or synbiotic composition will further comprise a non-bovine protein, non-bovine lipid, non-bovine carbohydrate, or other non-bovine component.

The dosages of the prebiotic and synbiotic compositions of the present invention will be varied depending upon the requirements of the individual and will take into account factors such as age (infant versus adult), weight, and reasons for loss of beneficial gut bacteria (e.g., antibiotic therapy, chemotherapy, disease, or age). The amount administered to an individual, in the context of the present invention should be sufficient to establish colonization of the gut with beneficial bacteria over time. The size of the dose also will be determined by the existence, nature, and extent of any adverse side-effects that may accompany the administration of a prebiotic or synbiotic composition of the present invention. In some embodiments, the dosage range will be effective as a food supplement and for reestablishing beneficial bacteria in the intestinal tract. In some embodiments, the dosage of a oligosaccharide(s) ranges from about 1 micrograms/L to about 25 grams/L of oligosaccharides.

The prebiotic or synbiotic formulations of the invention can be administered to any individual in need thereof. In some embodiments, the individual is an infant or toddler. For example, in some embodiments, the individual is less than, e.g., 3 months, 6 moths, 9 months, one year, two years or three years old. In some embodiments, the individual is an adult. For example, in some embodiments, the individual is over 50, 55, 60, 65, 70, or 75 years old. In some embodiments, the individual is immuno-deficient (e.g., the individual has AIDS or is taking chemotherapy).

Exemplary bifidobacteria that can be included in the probiotic compositions of the invention include, but are not limited to, *B. longum* subsp. *infantis, B. longum* subsp. *longum, B. breve*, and *B. adolescentis*. The *Bifidobacterium* used will depend in part on the target consumer. Exemplary bifidobacteria dosages for probiotic formulations include, but are not limited to, $10^4$ to $10^{12}$ colony forming units (CFU) per dose. A further advantageous range is $10^6$ to $10^{10}$ CFU.

For example, in some embodiments, *B. longum* subsp. *infantis* is administered with the oligosaccharide compositions of the invention to an infant or young child (e.g., under 5 years old). In some embodiments, *B. longum* subsp. *infantis* is included in, or in conjunction with, an infant formula or follow-on formula. In some embodiments, the compositions are administered to an adult or an elderly person. In some embodiments, the person is at least 50, 60, 70, or 80 years old.

It will be appreciated that it may be advantageous for some applications to include other Bifidogenic factors in the formulations of the present invention. Such additional components may include, but are not limited to, fructoligosaccharides such as Raftilose (Rhone-Poulenc, Cranbury, N.J.), inulin (Imperial Holly Corp., Sugar Land, Tex.), and Nutraflora (Golden Technologies, Westminister, Colo.), as well as lactose, xylooligosaccharides, soyoligosaccharides, lactulose/lactitol, among others. In some applications, other beneficial bacteria, such as *Lactobacillus*, can be included in the formulations.

In some embodiments, the compositions of the invention are administered to a human or animal in need thereof. For example, in some embodiments, the compositions of the invention are administered to a person or animal having at least one condition selected from the group consisting of inflammatory bowel syndrome, constipation, diarrhea, travelers diarrhea, antibiotic-induced diarrhea, *Clostridium difficile* infections (CDI), enteritis, colitis, Crohn's disease, colon cancer, allergic reaction, functional bowel disorder (FBD), irritable bowel syndrome (IBS), irritable bowel disease (IBD), excess sulfate reducing bacteria, inflammatory bowel disease (IBD), Autism Spectrum Disorder (ASD), necrotizing enterocolitis (NEC), and ulcerative colitis. Irritable bowel syndrome (IBS) is characterized by abdominal pain and discomfort, bloating, and altered bowel function, constipation and/or diarrhea. There are three groups of IBS: Constipation predominant IBS (C-IBS), Alternating IBS (A-IBS) and Diarrhea predominant IBS (D-IBS). The compositions of the invention are useful, e.g., for repressing or prolonging the remission periods on Ulcerative patients. The compositions of the invention can be administered to treat or prevent any form of Functional Bowel Disorder (FBD), and in particular Irritable Bowel Syndrome (IBS), such as Constipation predominant IBS (C-IBS), Alternating IBS (A-IBS) and Diarrhea predominant IBS (D-IBS); functional constipation and functional diarrhea. FBD is a general term for a range of gastrointestinal disorders which are chronic or semi-chronic and which are associated with bowel pain, disturbed bowel function and social disruption.

In another embodiment of the invention, the compositions of the invention are administered to those in need stimulation of the immune system and/or for promotion of resistance to bacterial or yeast infections, e.g., Candidiasis or diseases induced by sulfate reducing bacteria, *Enterococcus faecalis, Clostridium difficile, Clostridium perifringens, Salmonella enterica, Vibrio cholerae, E. coli* O157:H7, *Listeria monocytogenes, Yersinia entercolitis, Enterococcus faecalis, Eubacteria rectales*, other enteropathogenic bacteria, or *Shigella* species in the gut, thereby reducing colonization of the gut by at least one of the above-listed bacteria.

In some embodiments, the compositions comprising the oligosaccharides described herein (e.g., in Table 1 or otherwise purified from bovine milk) are administered to an individual, thereby increasing gut colonization and persistence of probiotic bacteria in the individual. In some embodiments, the compositions comprising the oligosaccharides described herein (e.g., in Table 1 or otherwise purified from bovine milk) are administered to an individual, thereby selectively stimulating production of probiotic (including but not limited to Bifidobacterial) secretions in the individual. Examples of such secretions include, but are not limited to antibiotics, bacteriocins, or other modulators of gut health.

In some embodiments, the compositions comprising the oligosaccharides described herein (e.g., in Table 1 or otherwise purified from bovine milk) are administered to an individual, thereby improving biomarkers of gut health in the individual. Examples of biomarkers of gut health include, e.g., decrease in inflammatory cytokines and chemokines. Exemplary markers include, but are not limited to, IL-4, IL-1β, IL-6, TNF-α, IL-1β and INF-γ.

IV. Modification of BMOs

Analysis of the compositional and structural data of bovine milk oligosaccharides (BMOs) (Table 1) has surprisingly revealed that these compositions can be further manipulated to create structures identical to oligosaccharides found in human milk. Thus, in some embodiments, one or more enzymatic reactions can be performed on one or more bovine milk oligosaccharides (e.g., as described in Table 1) to generate a modified oligosaccharide. In some embodiments, the modified oligosaccharides are identical to those that occur in human milk.

Alternatively BMOs, and especially those containing fucosylated and sialylated moieties, modified as described herein, or unmodified, can be added to existing oligosaccharide mixtures (including but not limited to GOS or FOS) to create classes of prebiotic oligosaccharide mixtures more closely mimicking HMO.

Analysis of the BMO monomeric composition (Table 1) has surprisingly revealed an oligosaccharide with m/z 730.25, having by 3 Hex and 1 HexNAc and a degree of polymerization (DP) of 4; and another one with m/z 1095.38, comprised by 4 Hex and 2 HexNAc and DP of 6, which are identical to two of the most abundant HMO structures from pooled human milk. Therefore BMO can be used as a useful source of at least two oligosaccharides previously only known to exist in human milk.

Additional HMO compositions can be generated by employing a fucosyltransferase and reacting a single monomeric unit of UGD-Fucose with the BMO with a m/z 730.25 and 1095.38. Yet another useful composition of HMOs can be obtained from a BMO substrate by addition of a single HexNAc-Fuc dimer by the action of a glycosyltransferases to BMO with m/z 892.34 and 1257.42.

Yet another useful composition can generated by employing a fucosyltrasferase and adding one, two or several GDP-Fucose moieties to the HexNAc termini of BMO, thereby generating HMO analogues and fucosylated-BMO (f-BMO) compositions. In some embodiments, these modified oligosaccharides are added to existing oligosaccharide mixtures (including but not limited to GOS or FOS).

Another useful composition can be generated by using a sialyltrasferase and adding one, two or several CMP-Sialic Acid to the HexNAc termini of BMO to generate sialylated-BMO (s-BMO) compositions. In some embodiments, these modified oligosaccharides are added to existing oligosaccharide mixtures (including but not limited to GOS or FOS).

Another useful composition can be generated by enzymatically cleaving from BMO a dimer comprised of HexNAc-Fuc. In some embodiments, these modified oligosaccharides are added to existing oligosaccharide mixtures (including but not limited to GOS or FOS).

EXAMPLES

The following examples are offered to illustrate, but not to limit the claimed invention.

Example 1

Matrix-Assisted Laser Desorption/Ionization Fourier Transform-Ion Cyclotron Resonance Mass Spectrometry (MALDI FT-ICR MS) Analysis of Oligosaccharides in Bovine Milk Oligosaccharide analysis was performed using a ProMALDI-FT-ICR mass spectrometer (IonSpec, Lake Forest, Calif.) equipped a 7.0 Tesla superconducting magnet, hexapole ion accumulation, and fitted with a 355 nm pulsed Nd:YAG laser. This instrument is well-known for high mass accuracy (<10 ppm with external calibration) and high resolution (>100 000 full width at half-height). This means that oligosaccharides are readily identified solely based on their mass. The exact composition with regard to hexoses, N-acetylhexosamines, sialic acids, and fucoses are now known and determined from the accurate masses. Samples were crystallized using 2,5-dihydroxybenzoic acid as matrix (5 mg/100 μL in a solution of 50% acetonitrile/50% water (v/v)). The solution of oligosaccharide (1 μL) was applied to the MALDI probe followed by addition of 0.01 M NaCl (0.5 μL) and the matrix solution (1 μL). Sample spots were dried by a technique similar to fast evaporation method prior to mass spectrometric analysis. Spectra were acquired in the positive-ion mode and internally calibrated (FIG. 1).

Most glycan tandem mass spectra are produced by collisional induced dissociation (CID), a tandem technique in which selected precursor ions are dissociated by collision with gas atoms in a collision cell. The collisions increase the vibrational energy of the ions to the point that bond rupture occurs revealing the monosaccharide composition.

Tandem MS was performed to obtain information about the monomeric composition. using sustained off resonance irradation (SOR1) collisional-induced dissociation (CID) to determine the composition and putative structure of each oligosaccharide (Table 1). The precursor ion was isolated and excited to 1000 Hz of their cyclotron frequency at a SOR1 amplitude of 2.55 V. Nitrogen gas was used as the collision gas and was pulsed in to maintain a pressure of 10-6 Torr.

Comparative Analysis of SMO and HMO

Composition and putative structures of BMOs were identified by MALDI FT-ICR were compared to the complete list of HMO structures and compositions isolated from pooled human breast milk [16].

MALDI FT-ICR was used on bovine milk after removal of the glycosidase enzymes, and an example of the resulting mass spectrum is presented below as well as the monomeric composition and the relative abundance. By means of the glycosidase enzymes removal we were able to discover the presence of 24 high-molecular weight ions from DP 7 to DP 10 never observed before in bovine milk (FIG. 1). All the 24 new peaks resulted to be milk oligosaccharides, and 6 contained fucose on their terminus, a monomer previously not reported in bovine milk high molecular weight oligosaccharides (Table 1). This invention describes the use of novel BMO formulations and their derivatives, to modulate the composition of mammalian microbiomes and positively impact health.

BMO a New Class of Prebiotic Substrates

Figure 2:
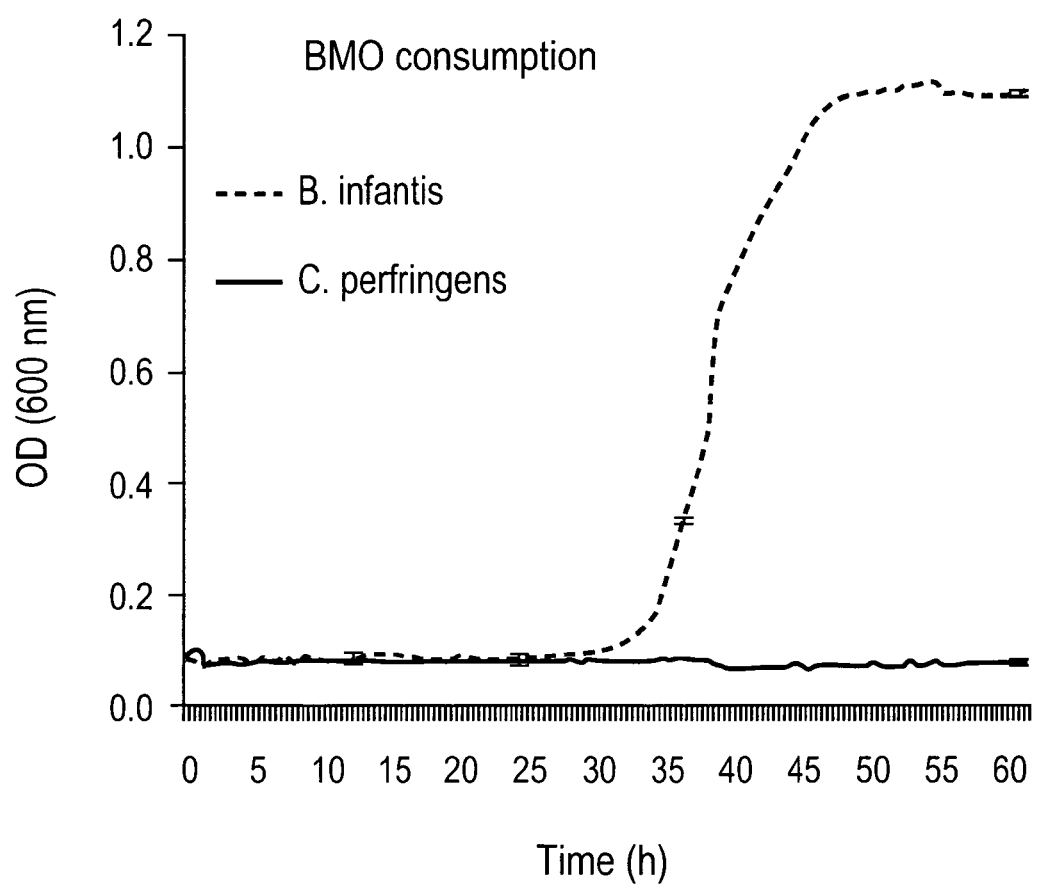
FIG. 2 illustrates growth of B. infantis and Clostridium perfringens on bovine milk oligosaccharides (BMO).
Figure 3A:
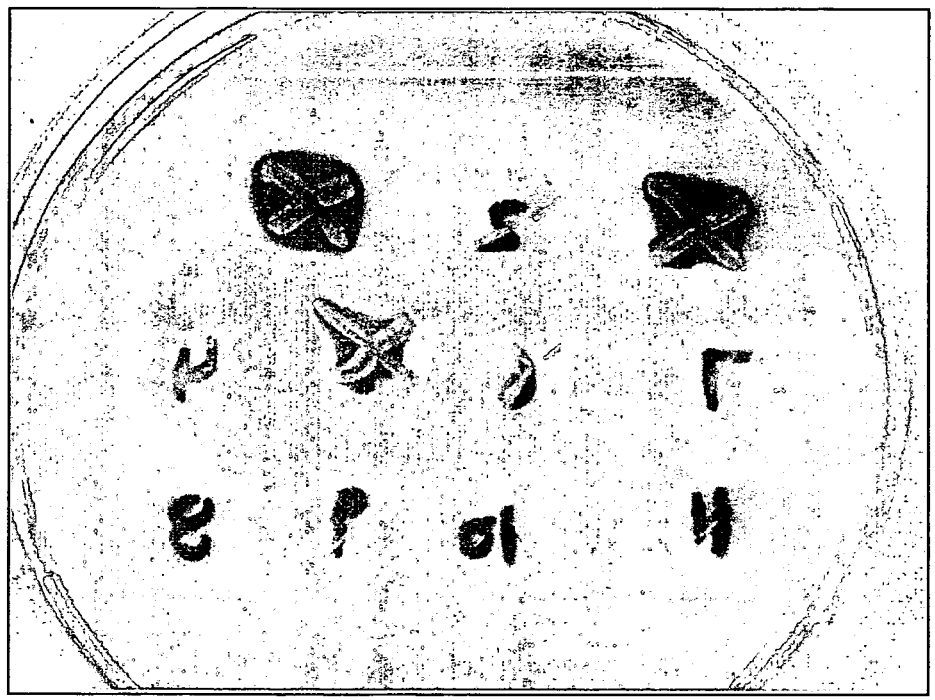
FIG. 3A) Lactose—MacConkey plate, growth observed for Salmonella with a lac operon insertion and the lac operon positive E. coli, growth represented by the red strikes on the BMO-Agar plate, as shown in 1,3,5.
Figure 3B:
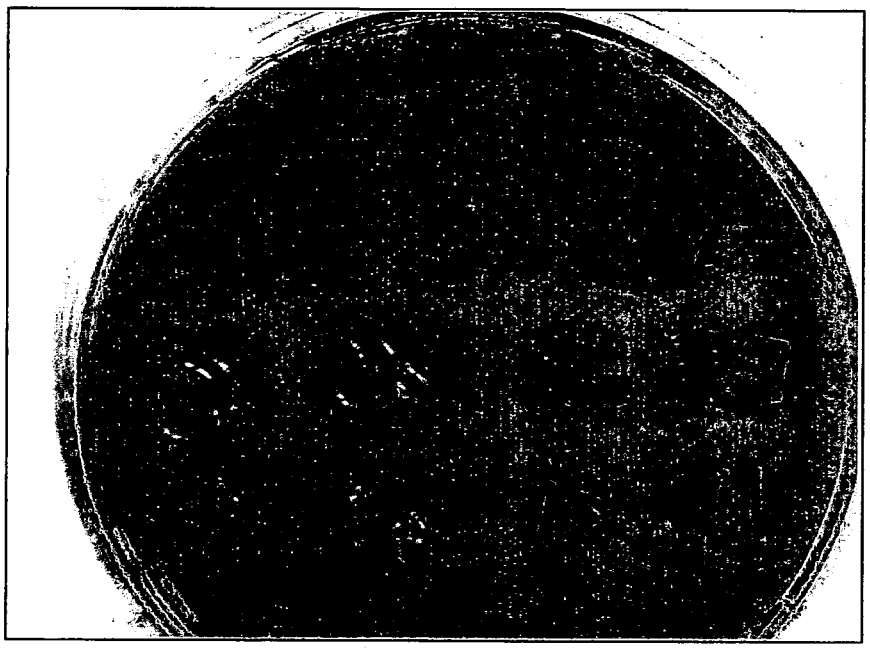
FIG. 3B) BMO—MacConkey (2 g per 100 ml) growth observed for Salmonella with a lac operon insertion and the lac operon positive E. coli, growth represented by the red strikes on the BMO— MacConkey Agar plate, as shown in 1,3,5. The Lac operon permease can transport BMO trimers and tetramers. Yersinia enterocolitica was negative on lactose and modestly positive on BMO, all other bacteria were negative on both media. BMOs were suspended at 1 gr/10 mL of sterile water, 10 N NaOH was added until the pH was 7. The BMO solution was used in a MacConkey medium to generate agar plates.
1. E. coli K12
2. E. coli K12 (DH5alpha, lac minus)
3. E. coli O157:H7
4. Salmonella typhimurium
5. Salmonella typhimurium+lac operon
6. Salmonella typhimurium
7. Salmonella typhimurium
8. Listeria monocytognes
9. Yersinia enterocolitica
10. Vibrio cholerae
11. Vibrio cholerae

Testing of strict anaerobes indicated that BMOs promote vigorous growth of *B. infantis* (FIG. 2) and little or no growth of the pathogen *Clostridium perfringens* (FIG. 3A). Importantly, we also found that clinical isolates of the facultative anaerobes *Salmonella enterica* seovar *Typhimurium* and *Vibrio cholerae*, *E. coli* O157:H7 lacked the ability to utilize BMO (FIG. 3B). Other significant enteropathogenic bacteria,

*Shigella* species, and other serotypes of *Salmonella* and *V. cholerae, Listeria monocytogenes, Yersinia entercolitis, Enterococcus faecalis, Eubacteria rectales* are also not expected to grow on BMO. Thus BMO promoted growth of a primary beneficial bacterium without metabolic enhancement to three pathogenic agents, two of which cause considerable morbidity to humans in developing countries worldwide. This data positions BMO as a more suitable mimic of HMOs than the current collection of commercial prebiotics being added to infant formula. Given the significant portion of fucosylated BMO that were discovered in bovine milk and dairy products and dairy by-products (such as cheese whey streams, whey protein concentrate, whey permeate, whey protein isolate), these fractions are likely effective in binding and deflection of enteric pathogens.

Example 2

Use of BMO Composition to Select Optimal Probiotic Strains

There are no commercially available probiotics specifically developed to consume BMOs as a prebiotic substrate. BMO can be used to identify and screen putative probiotic strains by using a novel approach based on milk oligosaccharides as a means for enrichment, isolation and efficacy. This approach can create a panel of probiotic strains that could be delivered in conjunction with BMO as a single synbiotic application, and enhance intestinal persistence and probiotic efficacy. Thus, in some embodiments, bacteria are selected that can grow on one or more oligosaccharides from bovine milk as a sole carbon source.

Fecal enrichments using BMO as a sole growth substrate are an effective way to select for BMO+ microorganisms. To perform fecal enrichments [20] a newly developed chemically-defined media ZMB1 [21] can used containing BMO as a sole carbon source. A 0.5 mL aliquot of ZMB1+BMO (2%) is inoculated with feces from healthy breast-fed infants (0.001% inoculum) and allowed to grow for 24 hrs and the culture transferred to a new 0.5 mL aliquot. This process is repeated a total of 4 times. To obtain emergent bifidobacterial isolates, the final enrichments are be plated on bifidobacterial selective media [22]. Cells from putative bifidobacterial colonies are examined microscopically to confirm bifid cell shape and screened for the presence of the fructose-6-phosphate phosphoketolase, a enzyme uniquely present in bifidobacteria [23]. Putative bifidobacterial colonies are replica-plated and cell forming units are counted after incubation in an anaerobic chamber at 37° C. for 1-7 days.

Bifidobacterial colonies are transferred to grid plates and screened by genus specific PCR [24]. Colonies positively identified as bifidobacteria are transferred to microtiter plates containing 150 uL BMO-ZMB1, 50 uL of sterilized mineral oil, and grown for 24-96 hrs at 37° C. anaerobic chamber and stored at -80° C. Isolates that exhibit different morphology are picked from the plate with the goal of obtaining the greatest diversity of BMO+bifidobacterial species and isolates. Once colonies are stored they are re-streaked on MRS media and further characterized by 16S rDNA sequencing for species classification, and at the subspecies level by Multi Locus Sequence Typing (MLST).

Strains isolated from the fecal enrichments are typed by sequence analysis of 16S ribosomal (rDNA) sequences, and MLST [25] a molecular typing method that has used to type closely related bifidobacteria at the subspecies level. PCR is used to amplify intragenic regions of seven housekeeping genes (e.g., clpC, dnaB, dnaG, dnaJ1, purF, rpoC, xfp) with primers from a comparative genomics study of bifidobateria [26]. The resulting sequencing data for the loci are aligned using the CLUSTAL W algorithm, and concatenated prior to phylogenetic analysis with MEGA 4.0 [27]. Allelic sequences are assigned as described previously [27]. This analysis generates a strain-level and subspecies-level taxonomical classification for BMO+ bifidobacteria isolated from the fecal enrichment studies.

Use of BMO to Select Optimal Strains Based on Growth Kinetics

After the fecal enrichment step the growth kinetics of BMO+ bifidobacteria is determined, and those strains that optimally consume BMO can be selected by this screening method. This can be accomplished by using methods known in the art for example using a high throughput method to measure growth kinetics of HMO+ bifidobacteria, employing a microtiter plate growth assays in an anaerobic environment [28]. This method was used to test the growth of *B. infantis* ATCC 15697 on BMO and vigorous growth was observed, however there was a significant lag time before active growth. Thus this assay can be useful to identify improved strains that (a) consume BMO at a faster rate and grow to a higher optical density and (b) more quickly adapt to BMO growth (i.e. less lag time). Data generated by the growth studies is then analyzed to calculate the growth kinetics for each strain and select optimal candidate strains.

For example, supernatants are collected at the beginning and end of the high-throughput growth studies, filter-sterilized (0.45 µm filter) and heat-inactivated (100° C. for 5 min.). BMOs are isolated by solid-phase extraction using graphitized carbon, the relative concentration of individual BMOs are obtained by MALDI-FTICR-MS as previous described [28]. The comparison between the two time points indicates bacterial consumption of the prebiotic substrate. The mass spectra are computed and analyzed to generate the consumption glycoprofiles. The following factors are taken into consideration to guide in the selection of strains with optimal BMO consumption capacity: growth kinetics, BMO consumption glycoprofile, production of bacteriocins, and taxonomic position (i.e. within infant-associated Glade). BMO+ bifidobacteria belonging to one of the recognized infant-clades (*B. longum* sbsp. *infantis, B. breve, B. bifidum*), and exhibiting superior outcomes in these phenotypes are considered the preferred candidates in some embodiments for a synbiotic formulation containing BMO and cognate probiotic strains.

Symbiotic Formulations Containing BMO and Probiotic BMO+ Strains

It is expected that the combination of BMO and select infant-borne bifidobacteria can prime the establishment of a protective microbiota typical of healthy, breast-fed infant. A synbiotic product comprising BMO+ bifidobacteria and a relevant dose of BMOs can be administered to prevent infectious diarrhea in high-risk infants with compromised GIT function. Examples of high-risk infant populations are premature and immunocompromised infants, or infants with a short-gut following surgery for necrotizing enterocolitis, children with autism spectrum disorders. These pediatric populations often suffer recurrent GIT microbiota imbalances leading to frequent diarrheal episodes and other forms of GI distress [18]. Probiotic treatment—often employing cultures of lactobacilli or bifidobacteria delivered in dairy foods—has been linked to beneficial health outcomes in a variety of disease states including reduction in diarrhea [29], prevention of necrotizing enterocolitis [30], treatment of irritable bowel syndrome [31], treatment of IBD, and allergic reactions [32]. Given their long history of safe use and GRAS status, probiotic strains selected for the ability to optimally consume BMOs are expected to colonize and persist in the host thus improving their efficacy and imparting benefits to the host. Formulations of BMO and Bifidobacteria are useful therefore addressing many gastrointestinal, and immunological-based health concerns in human, pediatric and other mammalian populations.

Use of BMO to Select Bifidobacteria with Antimicrobial Production Capacity

It has been demonstrated that bacterocin production is one means by which probiotic bacteria colonize the intestine and reduce the presence of pathogenic strains [33]. Bifidobacteria secretions are dependent on the carbon source used to supplement the growth media. BMO compositions can be useful to mimic HMO and induce the secretion of bacteriocins. In that regard, probiotic strains from culture collections or fecal enrichments are grown on BMO and the supernatants screened for bacteriocin activity. For example, a simple agar diffusion assay [34] can be used. Inhibitory activity of these supernatants is screened against *Enterococcus faecalis, Clostridium difficile, Clostridium perifringens, Listeria monocytogenes, Yersinia entercolitis, Enterococcus faecalis, Eubacteria rectales* and *Salmonella enterica*, and other common enteric pathogens.

Use of BMO for Improvement of Biomarkers for Gut Health

Growth of Bifidobacteria spp. on HMOs results in increased binding to intestinal cells. It is expected that BMOs, given their structural similarities to HMOs, can increase binding of Bifidobacteria to Caco-2 cells. To test this effect standard adhesion experiments are performed on Bifidobacteria strains grown on BMO, or lactose as control, and real time PCR is used to enumerate microbial/Caco-2 cell binding [35]. In addition, transwell culture inserts are used to assess the ability of microbes to affect epithelial permeability or translocate across colonic epithelial monolayers [36].

It is well established that intestinal epithelial cells have cell surface and intracellular receptors that recognize and initiate cellular signaling in response to the presence of commensal bacteria and/or bacterial products [37] A number of probiotic species have been shown to promote tight junctional barrier function after disruption induced by either enteropathogenic *E. coli*, chemically-induced damage (eg TNBS-induced colitis, a common rodent model of inflammatory bowel disease) and also cytokine-induced damage. To assess effects of BMO-grown probiotics on monolayer resistance, cells are measured for transepithelial electrical resistance. For example, cells are mounted into eight-well gold microelectrode chambers for measurement of transepithelial electrical resistance (TER) using a real-time electric cell-substrate impendance sensing (ECIS) system (Applied BioPhysics, Troy, N.Y.). To determine whether BMO-grown probiotics are effective in preventing monolayer disruption by IFN-γ or TNF-α, monolayers are be preincubated for 2 h with the bacterium, followed by the addition of either IFN-γ (10 ng/ml) or TNF-α (10 ng/ml) to the serosal chamber. Additionally, to access the role of MAPK, the ERK inhibitor PD-98059 (25 uM) is added to the apical surface 15 min prior to the incubation with BMO-grown probiotics. Resistance will be measured with a voltohmeter following 24 h incubation. Measurements will be expressed as ohms per centimeter squared.

Real time RT-PCR is used to assess cytokine mRNA levels for IL-4, IL-1β IL-6, TNF-α, IL-1β and INF-γ in Caco-2 cells incubated with BMO-grown probiotics at the specific collection periods. Total RNA is isolated from scrapings of Caco-2 cells and used to generate cDNA using random primers. The relative level of cytokines will be assessed in individual reactions using gene-specific primers and dual-labeled probes as described previously [36,38]. The inflammation indicators IL-6 and IL-1β will be measured using primers according to Newborg et al. [4].

Use of BMO to Enhance Gut Colonization and Persistence of Probiotics

Several different levels of BMO are formulated into the standard mouse chow diet with lactose and chow containing no added milk sugar as control chows. Colonization/persistence of *B. infantis* in the mouse intestine are be scored by examination of fecal DNA using strain specific quantitative PCR followed for four weeks. The impact of *B. infantis*/MOs on the complete mouse intestinal microbiota are be examined by specific QPCR of *B. infantis* ATCC15697 and pyrosequencing of amplified V1-V3 region of the 16S rDNA genes obtained from the fecal DNA Use of BMO to Deflect Infection by *Salmonella typhimurium*

Mouse models of acute (BALB/c, Nramp1−/− mice) and chronic (129×1/SvJ, Nramp1+/+mice) salmonellosis provide an ideal avenue for testing the ability of BMOs to promote protection and/or clearance of infection. These infection models are used to evaluate whether mice fed BMOs with or without *B. infantis* are more resistant to oral infection by *S. Typhimurium*. Bacterial colonization of gastrointestinal tissues following oral infection is assessed by real time PCR. For the chronic model of salmonellosis, the administration of BMO with or without *B. infantis* is evaluated to assess whether this supplementation promotes pathogen clearance or reduces intestinal inflammation. Quantification of pathogen load in tissues are assessed by real time PCR, histological evaluations of the infected tissues provide information on the pathology and progression of the infection, and chemokine/cytokine profiling are used to measure the host immunological response.

Use of BMO to Prevent and Treat Autism Spectrum Disorders (ADS)

It has been recently proposed that a dysbiosis in gut microbiota could influence the host capacity to process intestinal and urinal xenobiotics with a potential role in early brain development and autism disorders [39] ADS children are deficient in their detoxification capacity, and the sulfoconjugation of dietary derived phenolic amines, which can pass the blood-brain barrier negatively affect the function of neurotransmitters and the central nervous system [40]. The host microbiota is known to metabolize protein-derived phenolic amines, such as phenylalanine and tyrosine to form the urinary metabolites phenylacetylglutamine, 4-cresol sulfate. Other urinary metabolites like taurine, hyppurate, N-methyl nicotinic acid, N-methyl nicotinamide are altered in ADS children [39], and can be used as a biomarkers for measuring the effectiveness of BMO-based therapy to prevent and treat ADS.

Compared to their nonautistic siblings, the fecal microbiome of ADS children contain increased diversity of the sulfate-reducing *Clostridia* spp. and higher cell counts of *Clostridium histolyticum* group [41, 42]. High levels of *Clostridia* spp. could therefore further strain the already compromised sulfoconjugation and detoxification capacity of ADS children, and the excess toxins could negatively impact the central nervous system.

In some embodiments, compositions comprising the BMOS described herein are used to displace and decrease levels of *Clostridia* spp. colonic populations in ADS children by BMO and Bifidobacteria spp. supplementation. presence of *Clostridia* spp. Decreasing the population of *Clostridia* spp. in ADS children can be achieved by administering a BMO+*Bifidobacterium* spp strain with high capacity of colonic persistence through time.

REFERENCES

[1] Ninonuevo, M. R., et al., A Strategy for Annotating the Human Milk Glycome. Journal of Agricultural and Food Chemistry, 2006. 54(20): p. 7471-7480.
[2] Chaturvedi, P., et al., Survival of human milk oligosaccharides in the intestine of infants, in Bioactive Components of Human Milk Milk. 2001. p. 315-323
[3] Roberfroid, M., Prebiotics: The concept revisited. Journal of Nutrition, 2007. 137(3): p. 830s-837s
[4] Newburg, D. S., G. M. Ruiz Ruiz-Palacios, and A. L. Morrow, Human milk glycans protect infants against enteric pathogens. Annual Review of Nutrition, 2005. 25: p. 37-58.
[5] Harmsen, H. J. M., et al., Analysis of intestinal flora development in breast breast-fed and formula formula-fed infants by using molecular ide identification and detection methods. Journal of Pediatric Gastroenterology and Nutrition, 2000. 30(1): p. 61-67.
[6] Favier, C. F., et al., Molecular monitoring of succession of bacterial communities in human neonates. Applied and Environmental Microbiology, 2002. 68(1): p. 219-226.
[7] LoCascio, R. G., et al., Glycoprofiling of Bifidobacterial Consumption of Human Milk Oligosaccharides Demonstrates Strain Specific, Preferential Consumption o of Small Chain Glycans Secreted in Early Human Lactation. Journal of Agricultural and Food Chemistry, 2007. 55(22): p. 8914-8919
[8] Favier, C. F., W. M. de Vos, and A. D. L. Akkermans, Development of bacterial and bifidobacterial communities in feces of newborn babies. Anaerob Anaerobe, 2003. 9(5): p. 219-229.
[9] Parracho M R T, O Bingham Max, Gibson G. R. and McCartney A. L. 2005. Differences between the gut microflora of children with autistic spectrum disorders and that of healthy children, J Med Microbiol 54, pp 987-991
[10] Girard, M. P., et al., A review of vaccine research and development: human enteric infections. Vaccine, 2006. 24(15): p. 2732-50.
[11] Ball, T. M. and A. L. Wright, Health care costs of formula formula-feeding in the first year of life. Pediatrics, 1999. 103(4): p. 870-876.
[12] Quigley, M. A., Y. J. Kelly, and A. Sacker, Breastfeeding and hospitalization for diarrheal and respiratory infection in the United Kingdom Millennium Cohort Study. Pediatrics, 2007. 119(4): p. 837-42.
[13] Howie, P. W., et al., Protective effect of breast feeding against infection. BMJ, 1990. 300(6716): p. 11 11-6.
[14] Wold, A. E. and I. Adlerberth, Breast feeding and the intestinal microflora of the infant—implications for protection against infectious diseases. Adv Exp Med Biol, 2000. 478: p. 77-93.
[15] Journal Watch in Pediatric and Adolescent Medicine; Mar. 26, 2008
[16] Ninonuevo M. R., Perkins P. D, Francis J., Lamotte L. M., LoCascio R. G. G., Freeman S., Mills D. A., German J. B., Grimm R., Lebrilla C. B. "Daily Variations in Oligosaccharides of Human Milk determined by microfluidic chip and mass spectrometry" Journal of Agriculture and Food Chemistry 2008; 56(2); 618-626.
[17] Ruiz Ruiz-Palacios, G. M., et al., *Campylobacter jejuni* binds intestinal H(O) antigen (Fuc alpha 1, 2Gal beta 1, 4GlcNAc), and fucosyloligosaccharides of human milk inhibit its binding and infection. Journal of Biological Chemistry, 2003. 278(16): p. 14112-14120
[18] Narayanan, I., K. Prakash, and V. V. Gujral, The value of human milk in the prevention of infection in the high-risk low-birth-weight infant. J Pediatr, 1981. 99(3): p. 496-8.
[19] Boehm, G. and Stahl, B. (2007) Oligosaccharides from milk. J. Nutr. 137, 847S-849S
[20] Collado, M. C. and Y. Sanz, Method for direct selection of potentially probiotic *Bifidobacterium* strains from human feces based on their acid-adaptation ability. J Microbiol Methods, 2006. 66(3): p. 560-3.
[21] Zhang, G., D. A. Mills, and D. E. Block, Development of chemically defined media supporting high-cell cell-density growth of lactococci, entero enterococci, and streptococci., Appl Environ Microbiol, 2009. 75(4): p. 1080-7.
[22] Munoa, F. J. and R. Pares, Selective medium for isolation and enumeration of *Bifidobacterium* spp. Appl Environ Microbiol, 1988. 54(7): p. 1715 1715-8.
[23] [Orban, J. I. and J. A. Patterson Patterson, Modification of the phosphoketolase assay for rapid identification of bifidobacteria. J Microbiol Methods, 2000. 40(3): p. 221 221-4.]
[24] Roy, D. and S. Sirois, Molecular differentiation of *Bifidobacterium* species with amplified ribosomal DNA restriction analysis and alignment of short regions of the ldh gene. lysis Ferns Microbiology Letters, 2000. 191(1): p. 17 17-24.
[25] Cai, H., et al., Genotypic and phenotypic characterization of *Lactobacillus casei* strains isolated from different ecological niches suggests frequent recombination and niche specificity. Microbiology, 2007. 153(Pt 8): p. 2655-65
[26] LoCascio et al. Comparative genomic hybridization of *Bifidobacterium longum* strains indicates conservation of milk oligosaccharide utilization in subsp. *infantis*. Submitted to Applied and Environmental Microbiology, 2010
[27] Ventura, M., et al., Analysis of bifidobacterial evolution using a multilocus approach. Int Syst Evol Microbiol, 2006. 56(Pt 12): p. 2783 2783-92.
[28] LoCascio, R. G., et al., A versatile and scalable strategy for glycoprofiling bifidobacterial consumption of human milk oligosaccharides. Microbial Biotechnology, 2009. 3(10): p. 333.
[29] McFarland, L. V., Meta-analysis of probiotics for the prevention of antibiotic associated diarrhea and the treatment of *Clostridium difficile* disease. Am J Gastro Gastroenterol, 2006. enterol, 101(4): p. 812-22.
[30] Deshpande, G., S. Rao, and S. Patole, Probiotics for prevention of necrotising enterocolitis in preterm neonates with very low birthweight: a systematic review of randomised controlled trials. Lancet, 2007. 369(9573): p. 1614 1614-20.
[31] Haller, D., et al., Guidance for substantiating the evidence for beneficial effects of probiotics in chronic inflammatory bowel disease and the functional disorder irritable bowel syndrome. Journal of Nutrition, 2010. 140(3): p. 690S-7S]
[32] Furrie, E., Probiotics and allergy. Proc Nutr Soc, 2005. 64(4): p. 465 465-9]
[33] Corr, S. C., et al., Bacteriocin production as a mechanism for the antiinfective activity of *Lactobacillus salivarius* UCC118. Proc Natl Acad Sci USA, 2007. 104(18): p. 7617-21.
[34] Tagg, J. R. and A. R. McGiven, Assay system for bacteriocins. Appl Microbiol, 1971. 21(5): p. 943.

[35] Tao, N., et al., Bovine milk glycome. Journal of Dairy Science, 2008. 91(10): p. 3768-78.
[36] Kunz, C., et al., Oligosaccharides in milk of different species including man, rhesus monk monkey, cow and pig. ey, Faseb Journal, 1996. 10(3): p. 43284328-4328., 32.
[37] Ninonuevo, M. R R., et al., Methods for the quantitation of human milk oligosaccharides in bacterial fermentation by mass spectrometry. Analytical Biochemistry, 2007. 361 (1): p. 15-23.
[38] Xie, Y. M., et al., Method for the comparative glycomic analyses of O O-linked, mucin mucin-type oligosaccharides. Analytical Chemistry, 2004. 76(17): p. 5186-5197.
[39] Yap I. K., Angley M., Veselkov K. A., Holmes H., Lindon J. C. and Nicholson J. K. Urinary Metabolic Phenotyping Differentiates Children with Autism from Their Unaffected Siblings and Age-Matched Controls. J Prot Res, 2010, 9 (6), pp 2996-3004
[40] Alberti A., Pirrone P., Elia M., Waring R. H. and Romano C. 1999. Sulphation deficit in "low-functioning" autistic children: a pilot study. Biological Psychiatry. 46: 420-424.
[41] Finegold S. M. et al, Gastrointestinal microflora studies in late-onset autism. Clinical Infectious Diseases. 35: S6-S16, 2002.
[42] Parracho, H. M. et al, Differences between the gut microflora of children with autistic spectrum disorders and that of healthy children. J. Med. Microbiol. 54 (10), pp. 987-991, 2005.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A composition comprising an oligosaccharide from bovine milk or milk product and an inoculum of *Bifidobacterium longum* subsp. *infantis* or *B. breve*, wherein the oligosaccharide is selected from the group consisting of:
    an oligosaccharide consisting of 3 Hexose (Hex) moieties, 4 N-acetyl hexosamine (HexNAc) moieties and 1 fucose (Fuc) moiety;
    an oligosaccharide consisting of 4 Hex moieties, 4 HexNAc moieties, and 1 Fuc moiety;
    an oligosaccharide consisting of 5 Hex moieties, 4 HexNAc moieties, and 1 Fuc moiety;
    an oligosaccharide consisting of 4 Hex moieties, 5 HexNAc moieties, and 1 Fuc moiety;
    an oligosaccharide consisting of 3 Hex moieties, 6 HexNAc moieties, and 1 Fuc moiety;
    an oligosaccharide consisting of 3 Hex moieties and 6 HexNAc moieties,
    an oligosaccharide consisting of 4 Hex moieties and 3 HexNAc moieties;
    an oligosaccharide consisting of 3 Hex moieties and 4 HexNAc moieties;
    an oligosaccharide consisting of 6 Hex moieties and 2 HexNAc moieties;
    an oligosaccharide consisting of 4 Hex moieties and 4 HexNAc moieties;
    an oligosaccharide consisting of 3 Hex moieties and 5 HexNAc moieties;
    an oligosaccharide consisting of 5 Hex moieties and 4 HexNAc moieties;
    an oligosaccharide consisting of 4 Hex moieties and 5 HexNAc moieties; and
    an oligosaccharide consisting of 3 Hex moieties and 6 HexNAc moieties.

2. The composition of claim 1, comprising at least two oligosaccharides selected from the group consisting of:
    an oligosaccharide consisting of 3 Hex moieties, 4 HexNAc moieties and 1 Fuc moiety;
    an oligosaccharide consisting of 4 Hex moieties, 4 HexNAc moieties, and 1 Fuc moiety;
    an oligosaccharide consisting of 5 Hex moieties, 4 HexNAc moieties, and 1 Fuc moiety;
    an oligosaccharide consisting of 4 Hex moieties, 5 HexNAc moieties, and 1 Fuc moiety;
    an oligosaccharide consisting of 3 Hex moieties, 6 HexNAc moieties, and 1 Fuc moiety;
    an oligosaccharide consisting of 3 Hex moieties and 6 HexNAc moieties,
    an oligosaccharide consisting of 4 Hex moieties and 3 HexNAc moieties;
    an oligosaccharide consisting of 3 Hex moieties and 4 HexNAc moieties;
    an oligosaccharide consisting of 6 Hex moieties and 2 HexNAc moieties;
    an oligosaccharide consisting of 4 Hex moieties and 4 HexNAc moieties;
    an oligosaccharide consisting of 3 Hex moieties and 5 HexNAc moieties;
    an oligosaccharide consisting of 5 Hex moieties and 4 HexNAc moieties;
    an oligosaccharide consisting of 4 Hex moieties and 5 HexNAc moieties; and
    an oligosaccharide consisting of 3 Hex moieties and 6 HexNAc moieties.

3. The composition of claim 1, comprising one or more of
    an oligosaccharide consisting of 3 Hex moieties, 4 HexNAc moieties and 1 Fuc moiety;
    an oligosaccharide consisting of 4 Hex moieties, 4 HexNAc moieties, and 1 Fuc moiety;
    an oligosaccharide consisting of 5 Hex moieties, 4 HexNAc moieties, and 1 Fuc moiety;
    an oligosaccharide consisting of 4 Hex moieties, 5 HexNAc moieties, and 1 Fuc moiety;
    or an oligosaccharide consisting of 3 Hex moieties, 6 HexNAc moieties, and 1 Fuc moiety.

4. The composition of claim 1, wherein the inoculum is an inoculum of *Bifidobacterium longum* subsp. *infantis*.

5. The composition of claim 1, wherein the inoculum is an inoculum of *B. breve*.

6. The composition of claim 1, wherein the composition is a powder.

7. The composition of claim 1, wherein the oligosaccharide consists of 3 Hex moieties, 4 HexNAc moieties and 1 Fuc-moiety.

8. A method of obtaining oligosaccharides, the method comprising:
    purifying oligosaccharides from bovine milk or a bovine milk product, wherein the purifying comprises inactivating fucose-, sialic acid-, N-Acetylglucosamine-, lacto-N-biose-, glucose- and galactose-degrading enzymes in milk.

9. The method of claim 8, wherein the purified oligosaccharides comprise at least one or more oligosaccharides recited in claim 1.

10. A method of obtaining one or more of the oligosaccharides recited in claim 1, comprising purifying the oligosaccharide from bovine milk.

11. The method of claim 10, wherein the purifying comprises separating fucose-, sialic acid-, N-Acetylglucosamine-, lacto-N-biose-, glucose- and galactose-degrading enzymes in milk from the oligosaccharide.

12. A method of modifying the oligosaccharide of claim 1, comprising contacting the oligosaccharide with at least one modifying enzyme, thereby adding or removing one or more chemical moieties from the oligosaccharide, thereby generating a modified oligosaccharide.

13. The method of claim 12, wherein the modifying enzyme is selected from the group consisting of a fucosidase, fucosyltransferase, sialidase, sialyltransferase, a glycosidase, and a glycosyltransferase.

14. A method of treating a condition in an individual comprising administering an amount of the composition of claim 1 to the individual wherein the condition is selected from the group consisting of diarrhea; necrotizing enterocolitis; irritable bowel syndrome; allergic reaction; Autism Spectrum Disorder (ASD); and presence of *Enterococcus faecalis, Clostridium difficile, Salmonella enterica, Salmonella typhimurium, Vibrio cholerae, E. coli* O157:H7, *Clostridium perifringens, Vibrio cholerae, Listeria monocytogenes, Yersinia entercolitis, Enterococcus faecalis, Eubacteria rectales*, or *Shigella* species in the individual.

15. The method of claim 14, wherein the oligosaccharide selectively stimulates the production of a Bifidobacterial secretion that modulates gut health in the individual; improves at least one biomarker of gut health in the individual; or increases gut colonization and persistence of probiotic bacteria.

\* \* \* \* \*